United States Patent [19]

Hanausek-Walaszek et al.

[11] Patent Number: 5,310,653
[45] Date of Patent: May 10, 1994

[54] TUMOR MARKER PROTEIN AND ANTIBODIES THERETO FOR CANCER RISK ASSESSMENT OR DIAGNOSIS

[75] Inventors: Margaret Hanausek-Walaszek, Bastrop; Thomas J. Slaga, Austin; Zbigniew Walaszek, Bastrop, all of Tex.

[73] Assignee: Board of Regents, The University of Texas System, Austin, Tex.

[21] Appl. No.: 12,972

[22] Filed: Feb. 2, 1993

Related U.S. Application Data

[63] Continuation of Ser. No. 426,408, Oct. 24, 1989, abandoned.

[51] Int. Cl.$^5$ .................. G01N 33/574; A61K 39/00; A61K 37/08; C07K 15/18
[52] U.S. Cl. ................... 435/7.23; 435/7.92; 424/88; 530/358; 530/387.7; 530/388.8; 530/389.7
[58] Field of Search ............... 435/7.23, 7.92; 424/88; 530/387.7, 388.8, 389.7, 358

[56] References Cited

U.S. PATENT DOCUMENTS 4,448,890 5/1984 Smetana et al. ............... 436/508
4,746,539 5/1988 Webb et al. ................... 424/88

OTHER PUBLICATIONS

Hamausek-Walaszek et al., Progress in Clinical and Biological Research (1989).
Hanausek-Walaszek et al., "Carcinogenesis", Proceedings of the American Association for Cancer Research 30:190, Abstract 754 (1989).
Larroya et al., "Immunology", Proceedings of the American Association for Cancer Research 30:349, Abstract 1385 (1989).
Hanausesk-Walaszek et al., "Carcinogenesis", Proceedings of AACR 29:167, Abstract 665 (1988).
Hanausek-Walaszek et al., "Correspondence Between Biochemical and Antigenic Activity of a 60 Kilodalton Oncofetal Protein During Carcinogenesis and Tumorigenesis," Cancer Letters 33:55-61 (1986).
Hanausek-Walaszek et al., "A 60 Kilodalton Oncofetal Protein As Tumor Marker," J. Med. 17:13-23 (1986).

(List continued on next page.)

*Primary Examiner*—Christine M. Nucker
*Assistant Examiner*—M. P. Woodward
*Attorney, Agent, or Firm*—Arnold, White & Durkee

[57] ABSTRACT

A tumor-associated marker protein was purified and antibodies thereto developed for cancer diagnosis and assessment of cancer risk associated with the long-term use of synthetic steroid hormones, both contraceptive and non-contraceptive, and other drugs that exhibit tumor promotional properties. The marker protein and antibodies thereto provided are interspecies immunologically cross-reactive.

In summary, the marker p65 tumor-associated factor of the present invention has the following characteristics:
 (a) binds substantially completely to a phenyl hydrophobic interaction column in a buffer containing 20% ammonium sulfate and eluted at ca. 16% ammonium sulfate;
 (b) localized primarily in the nuclear envelopes with only small amounts present in the cytoplasm from where is released to the blood circulation in vivo or cell culture medium in vitro;
 (c) induced in normal, adult tissues by chemical carcinogens (initiators) but not by tumor promoters, the carcinogen-induced production being enhanced by the latter.

Also disclosed herein are processes for purifying the 65 kDa tumor marker from plasma, tumor cytosol or ascitic fluid of carcinoma bearing animals; processes for producing antisera and purified antibody preparations to the 65 kDa tumor marker; and methods using antibody to the 65 kDa to diagnose or assess the likelihood of cancer.

10 Claims, 1 Drawing Sheet

OTHER PUBLICATIONS

Schroder et al., "Proteins from rat liver cytosol which stimulate mRNA transport," Eur. J. Biochem. 159:51-59 (1986).

Hanausek-Walaszek et al., "Immunological Identity of a 60 KD Oncofetal Protein Induced in Rats by Chemical Carcinogens and Released by Transformed Cells," BBRC 127:779-785 (1985).

Hanausek-Walaszek et al., "Chemical carcinogens as specific inducers of a 60-kilodalton oncofetal protein in rats," Carcinogenesis 7:1725-1730 (1985).

Schumm et al., "Absence of the Cancer-associated Factor with a Molecular Weight of 60,000 from the Plasma of Patients with a Spectrum of Nonneoplastic Conditions," Cancer Res. 44:401-406 (1984).

Hanausek-Walaszek et al., "Characterization of a 60,000-dalton Oncofetal Protein from the Plasma of Tumor-Bearing Rats," Cancer Invest. 2:433-441 (1984).

French et al., "Nucleocytoplasmic Release of Pepetitive DNA Transcripts in Carcinogenesis Correlates with a 60 Kilodalton Cytoplasmic Protein," Cancer Letters 23:45-52 (1984).

Walaszek et al., "An Oncofetal 60-Kilodalton Protein in the Plasma of Tumor-Bearing and Carcinogen--Treated Rats," Cancer Letters 20:277-282 (1983).

Hanausek-Walaszek et al., "Structural and Immunological Identity of p, 65 Tumor-Associated Factors from Rat and Mouse Hepatocarcinomas," Progress in Clinical and Biological Ressearch (1989).

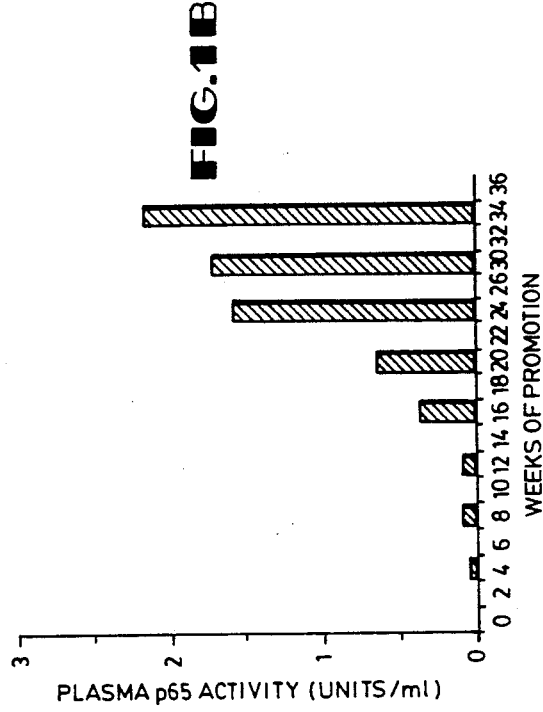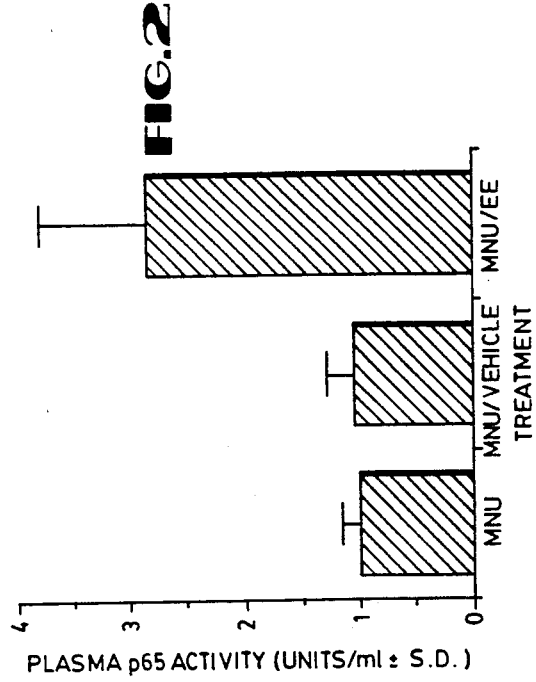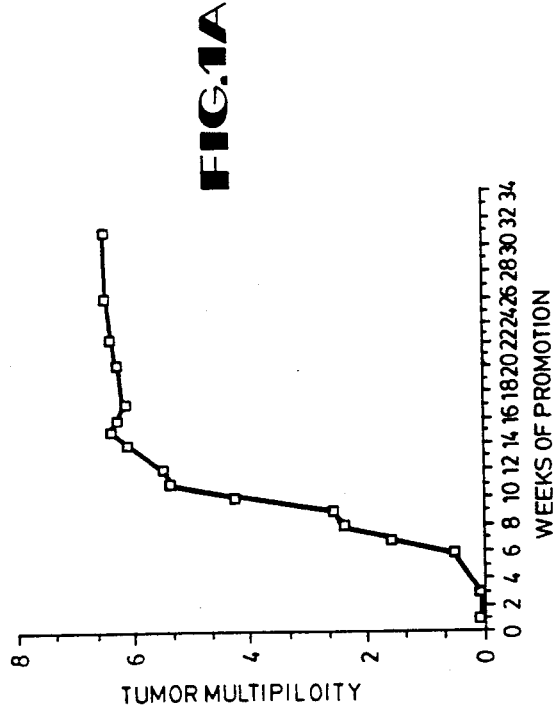

TUMOR MARKER PROTEIN AND ANTIBODIES THERETO FOR CANCER RISK ASSESSMENT OR DIAGNOSIS

GOVERNMENT RIGHTS

The United States Government may have certain rights to this invention pursuant to National Institutes of Health grant RR 5511-23.

This application is a continuation of application Ser. No. 07/426,408, filed Oct. 24, 1989 now abandoned.

FIELD OF THE INVENTION

This invention relates to the isolation and identification of a cancer associated protein, preparation of antibodies thereto, and methods of cancer risk assessment or diagnosis.

BACKGROUND OF THE INVENTION

In spite of improved treatments for certain forms of cancer, it is still a leading cause of death in the United States. Since the chance for complete remission of cancer is, in most cases, greatly enhanced by early diagnosis, it is very desirable that physicians be able to detect cancers before a substantial tumor develops. Also, in cases where the primary tumor has been substantially removed by surgery or destroyed by other means, it is important that the physician be capable of detecting any trace of cancer in the patient (either in the form of residues of the primary tumor or of secondary tumors caused by metastasis), in order that the physician can prescribe appropriate subsequent treatment, such as chemotherapy.

The quantities of cancer cells that must be detected for early diagnosis or following removal or destruction of the primary tumor are so small that the physician cannot rely upon physical examination of the cancer site. Moreover, in many cases the cancer site is of course not susceptible to direct visual observation and it is almost always impractical to detect secondary tumors by visual observation, since it is not possible to predict exactly where they are likely to occur. Accordingly, sensitive tests have to rely upon detection of cancer-associated materials, usually proteins, present in body fluids of patients who have, or are about to develop, cancer cells in their bodies. Several diagnostic materials for detection of cancer-associated proteins are available commercially. Tests for alpha-fetoprotein are used to detect primary liver cancer and teratocarcinoma in humans; and carcinoembryonic antigen is used for digestive system cancers, as well as lung and breast carcinomas; chorionic gonadotropin is employed to detect trophoblast and germ cell cancers; calcitonin is used for thyroid gland cancers; and prostatic acid phosphatase is used to detect prostate carcinoma. These markers are detectable in advanced rather than in early cancer.

Unfortunately, many of the commercially available tests are only applicable to a narrow range of cancer types, and therefore these tests suffer not only from the disadvantage that other types of cancer may be missed but also from the disadvantage that the narrow applicability of the tests means that it may be necessary to run multiple tests on a single patient for diagnostic purposes, a procedure which not only increases the expense of the diagnostic testing but also increases the risk that one or other of the tests may give a false positive result. Accordingly, there is a need for a single diagnostic test able to detect the presence of very small amounts of cells of a wide variety of different cancers. The ideal marker would be one that is specific and universal. Such a marker may exist if malignant transformation is associated with the expression of a unique gene product in all kinds of transformed cells.

It is already known that serum from the blood of animals suffering from a wide variety of cancers contains an oncofetal protein having a molecular weight of approximately 60,000 and having the capacity to increase the release of ribonucleic acid (RNA) from cell nuclei. This protein is referred to as oncofetal RNA-transport protein (ORTP) or 60 kDa cancer-associated protein.

ORTP is localized in the cytoplasm of tumors of humans and experimental animals and small amounts are released into the host circulatory system. The 60 kDa ORTP is notably absent from the nuclei of rat liver and rat liver tumors. It has been shown to be present in fetal rats at 18 days of gestation and in human and rat amniotic fluid, but not in maternal blood. It has not been detected in adult rats. Nor is it present in detectable concentrations in the blood of normal human subjects or those with a variety of non-neoplastic conditions or diseases, including benign tumors and other non-neoplastic proliferative diseases. In contrast, of more than 200 cancer patients with confirmed active disease, all tested positive for the factor. It was also present in all of about 200 tumor-bearing rats tested. Unfortunately, antibodies to a rat ORTP preparation purified as described in the prior art do not cross-react with human ORTP. Thus, the 60 kDa cancer marker proteins from different species are not immunologically equivalent, e.g., an antibody to the rat cancer marker protein does not cross-react with a human cancer marker protein. Thus, when the purified 60 kDa cancer marker protein preparation is to be used for production of antibodies for diagnostic purposes, it is necessary to begin the preparation process with plasma from the species in which the diagnosis is to be used.

We have recently identified and characterized another RNA-transport-stimulating oncofetal protein with a molecular weight of 65 kDa (p65) which exhibits certain properties which strongly favor its candidacy as a general tumor marker, as well as a marker of cancer risk associated with the prolonged use of drugs, such as androgenic and estrogenic hormones, that have tumor promotional potential.

SUMMARY OF THE INVENTION

This invention provides a protein preparation containing a relatively pure form of an oncofetal RNA-transport-stimulating cancer marker protein. More specifically, the invention provides a protein preparation comprising a cancer-associated protein having the following characteristics:

(a) not being precipitated by 30% saturated aqueous ammonium sulfate solution at 25° C.;

(b) molecular weight ca. 65,000±5,000, with some variation, as measured by electrophoresis on 12.5% SDS polyacrylamide slab gels;

(c) binds completely to a phenyl hydrophobic interaction column in a buffer containing 20% ammonium sulfate in 50 mM TrisCl, pH 7.5 with 1 mM EDTA and 10 mM 2-mercaptoethanol and is eluted by gradient when the ammonium sulfate concentration drops to ca. 16%;

(d) having a cyanogen bromide (CNBr) cleavage pattern of six major peptides with molecular weights of about 6, 9, 27, 39, 43 and 47 kDa;

(e) exhibiting interspecies immunological cross-reactivity, specifically the human p65 reacts with antibodies raised in rabbits directed against the rat p65 protein;

(f) present in only some lesions characterized by altered enzyme expression (i.e., those assumed to be precursors of malignant tumors) and presumably all malignant tumors but substantially absent from normal tissue, specifically absent from the maternal blood of non-cancerous normal mammals;

(g) localized primarily in the nuclear envelopes (but not within the nucleoli or intranuclear structures) with only small amounts present in the cytoplasm from where is released to the blood circulation in vivo or cell culture medium in vitro;

(h) induced in normal, adult tissues by chemical carcinogens (initiators) but not by tumor promoters, the carcinogen induced production being enhanced by the latter; and (i) having an RNA-releasing activity of at least about 10.0 units per milligram of total protein when assayed by the procedure set forth in column 4 of U.S. Pat. No. 4,746,539.

As used herein, the term "substantially" is a relative term meaning largely but not absolutely wholly as specified. The term allows for trace deviance from the absolute.

This invention also provides a process for preparing a purified cancer-associated protein, this process comprising:

(a) collecting from plasma, tumor cytosol or ascitic fluid of carcinoma-bearing animals or from culture medium in which cancer cells were grown, the protein fraction which is precipitated from plasma, tumor cytosol or ascitic fluid between 30% and 60% saturation of the aqueous ammonium sulfate solution or from culture medium at 90% saturation of the aqueous ammonium sulfate;

(b) dissolving the precipitate in a buffer at pH 7.5, chromatographing on a molecular sieving column and collecting a protein fraction having a molecular weight of about 65,000 daltons;

(c) separating the chromatographed fraction on a high performance liquid chromatography (HPLC) phenyl hydrophobic interaction column;

(d) purifying the collected 65,000 dalton protein fraction by electrophoresis on 12.5% SDS polyacrylamide gels; and (e) excising the protein fraction which appears at a mobility corresponding to a molecular weight of about 65,000 daltons.

This invention also provides an antibody preparation substantially free of antibodies to normal plasma fraction, and which antibody preparation is capable of forming an immunoconjugate with the instant p65 cancer-associated protein. The antibody preparation is capable of forming a visible precipitate with the cancer marker protein p65 when each is diffused toward one another in agar gel but is not capable of forming a conjugate with the 60 kDa ORTP derived from cytoplasm of tumors. Further, the antibody preparation exhibits interspecies cross-reactivity with other species derived 65 kDa tumor markers of this invention.

Finally, this invention provides a method for assessing the likelihood of cancer which involves immunoassays to detect the presence of the instant p65 tumor marker protein in biological material of a host suspected of developing cancer or being at high risk for developing cancer as the result of treatment with drug(s) known to have a tumor promotion potential.

BRIEF DESCRIPTION OF THE DRAWINGS

FIG. 1. p65 tumor-associated protein production during 7,12-dimethylbenz[a]anthracene (DMBA)-induced, and 12-O-tetradecanoylphorbol-13-acetate (TPA)-promoted skin carcinogenesis in SENCAR mice.

FIG. 1A shows the time course of papilloma appearance following carcinogenesis promotion and FIG. 1B shows the time course of p65 accumulation int he blood plasma following the same carcinogenesis promotion.

FIG. 2. Enhancement by synthetic steroid hormone of p65 tumor-associated protein production during chemical carcinogenesis.

DETAILED DESCRIPTION OF THE PREFERRED EMBODIMENTS

Methods for Diagnosing or Assessing the Likelihood of Cancer

Samples of blood plasma or serum tissue are obtained from human cancer patients or human subjects prior to and at different times in the course of treatment with synthetic steroid hormones or other drugs known or suspected of having a tumor promotion potential. Alternatively, samples of blood plasma, serum or tissue are obtained from other mammals suspected of suffering from cancer or treated with substances suspected of causing cancer.

Briefly, samples of the blood plasma or serum containing the same amount of protein are mixed with an electrophoresis sample buffer, boiled for three minutes and subjected to 12.5% SDS-PAGE. Subsequently, the gel slabs are prepared for transfer by equilibrating for one hour in 0.025M Tris, 0.192M glycine, 20% (v/v) methanol, pH 8.3, and then transblotted onto nitrocellulose sheets. To conduct the immunoassay, the nitrocellulose sheets are treated with appropriate blocking solution to block unspecific binding sites and incubated overnight, either with pre-immune serum (controls) or antibody against the p65 protein diluted 1:200. Secondary biotinylated antibody is applied next and the color is developed using ABC Elite Kit from Vector Laboratories, Burlingame, Calif. The highly specific polyclonal antibody against p65 is obtained by immunizing rabbit with pure human or rat p65 preparations. As an alternative, mouse monoclonal antibodies to p65 may be prepared using the techniques generally described in "Hybridoma Techniques" Cold Spring Harbor, N.Y., 1980, ISBN 0-87969-143-3.

The immunoblots are photographed and the bands of p65 immune complexes on the film are quantitated using a laser densitometer coupled to an integrator. Alternatively, following probing with the antibodies to p65 or pre-immune serum, nitrocellulose sheets are labeled with $^{125}$I-protein A. The labeled sheets are subjected to autoradiography followed by scanning the film with a laser densitometer coupled to an integrator. Another alternative is to use an ELISA procedure.

To interpret the plasma or serum or tissue samples, the relative quantity of p65 in the sample is indicated by the intensity of a band at nominal molecular weight about 65,000 as measured by laser scanning. Comparison with the corresponding area of the control (derived with the use of pre-immune serum) permits distinguishing response specific for p65 above non-specific background response. Specific activity of the marker band from clinical samples taken in the course of treatment is compared with the samples taken prior to treatment and/or with the average sample from a normal healthy pool. The clinical response can be then expressed as a factor against the response prior to treatment or against the response of the normal healthy pool, respectively. Steady increases in the value of clinical response over a period of time are indicative of an increased cancer risk associated with the long-term treatment with a given synthetic steroid or other drug that has tumor promotional properties. The high initial response is indicative of an existing cancer.

The following examples are given by way of illustration, without intent to limit the scope of the invention, to show details of particularly preferred reagents and techniques utilized in the processes of the instant invention.

EXAMPLE I

Animal Models for Determination of the Presence of Cancer Cells

This example illustrates the instant process for purification of the p65 tumor-associated protein and preparation of antibodies thereto as source of p65.

Rat and Mouse Liver Tumors

Rat hepatoma cell lines McA-RH7777 and McA-RH8994 were purchased from the American Type Culture Collection (Rockville, Md.) and carried as cell cultures in Swim's S77 medium with 4 mM L-glutamine and supplemented with 5% fetal calf serum and 20% horse serum (Gibco, Grand Island, N.Y.). After several passages in cell culture, rat hepatoma cells ($1 \times 10^6/0.2$ ml phosphate-buffered saline) were inoculated subcutaneously into a hind leg of male Buffalo rats (120–150 g) (Harlan Labs, Indianapolis, Ind.) and were carried as solid tumors according to conventional procedures.

Transplantable hepatocellular carcinoma (THC) 1682C was derived from primary hepatic tumors in ACI rats maintained for four months on the choline-deficient diet of Shinozuka containing 0.2% ethionine and eight months on a choline-supplemented (0.8%) diet without ethionine. THC T52 was established by intraperitoneal transplantation of growing tumors induced in ACI rats by 2-acetylaminofluorene (AAF). THC cultures were maintained in vitro and also carried as solid (1682C) and ascitic (T52) tumors in male ACI rats (The University of Texas M.D. Anderson Cancer Center Science Park-Veterinary Resources Division, Bastrop, Tex.).

The Reuber hepatoma cell culture H35 was provided by Dr. Andrew P. Butler, University of Texas M.D. Anderson Cancer Center Carcinogenesis Department, Science Park, Smithville, Tex.

Mouse liver carcinoma CRL 6421 (formerly NBL #MM45T.Li) was obtained from American Type Culture Collection and carried as cell cultures as described above for rat hepatoma cell lines.

Purification of p65

Preparation of the antibody involves purification of the p65 marker protein from the tissue culture medium of tumor cells of human or animal origin. Specifically, the cells were grown to confluence at 37° C. in the presence of media and a serum or serum-like supplement, or completely defined medium containing salts and hormones. Growing cells to confluence was a purely economical step which ascertains a high yield of the p65 marker protein. The preferred medium used was Dulbecco's Modified Eagle's Medium (DMEM) with 5% fetal calf serum and cells were grown in 5% $CO_2$. The confluent cells were washed three times in serum-free DMEM medium and incubated in this medium for 16–24 hours (the optimal time being 24 hours). At this point, medium was collected by centrifugation at $10,000 \times g$ for 10–15 minutes and treated with ammonium sulfate solution at 90% saturation of aqueous solution for 30 minutes at 4° C.

Protein precipitate was collected by 30-minute centrifugation at $10,000 \times g$, dissolved in a small volume of 50 mM TrisCl buffer, pH 7.5, with 50 mM NaCl, 10 mM 2-mercaptoethanol and 1 mM EDTA, and dialyzed overnight against the same buffer. After dialysis, proteins were loaded on an LKB TSK 3000 SW molecular sieving column and separated according to the molecular weight using an LKB HPLC system. Fractions containing proteins with molecular weight in the range of 50–90 kDa were collected and dialyzed overnight against buffer A, containing 20% ammonium sulfate in 50 mM Tris-Cl, pH 7.5 with 10 mM 2-mercaptoethanol and 1 mM EDTA.

Following dialysis, the 50-90 kDa proteins were loaded on a phenyl hydrophobic interaction column (PHI) (LKB, Pharmacia) equilibrated with buffer A. Generally, 800–1,000 ml of conditioned medium was processed as described above. The p65 marker protein weakly binds to the PHI column and is eluted in the first distinct peak by a gradient of 80% to 0% of buffer A, in combination with buffer B (50 mM Tris-Cl, pH 7.5 with 10 mM 2-mercaptoethanol and 1 mM EDTA, supplemented with 50% ethylene glycol). Fractions containing the p65 marker protein are then combined and dialyzed against buffer A devoid of ammonium sulfate, concentrated by lyophilization and electrophoresed on 12.5% SDS-PAGE at constant current of a 10 mA for two hours at room temperature.

Proteins are transblotted to a 0.22µ nitrocellulose sheet as described by Towbin et al. (Proc. Natl. Acad. Sci. U.S.A., Vol. 76, pages 4350–4353, 1979). A reversible ponceau A stain was used to visualize the nitrocellulose bound proteins according to the procedure of Salinovich and Montellaro (Anal. Biochem., Vol. 156, pages 341–347, 1986). The band of the p65 protein was cut out of the nitrocellulose sheets and used for immunization of rabbits.

Mouse p65 was isolated from the mouse liver carcinoma cell line CRL 6421 (MM45) and purified as described above for the rat factor.

Preparation of Antibodies to p65

Antisera to the purified rat p65 preparation were raised in rabbits, as follows.

Specific Pathogen Free (Pasteurella) male New Zealand white rabbits of approximately four kilograms body weight were used (Myrtle's Rabbitry). Pre-immune (day 0) and test blood samples (10 days following each of four immunizations on day 1, 14, 28 and 42) were obtained from the central artery of the ear or a lateral ear vein. The anesthetized rabbits were placed in sternal recumbency, the dorsal fur was removed with surgical clippers, and the surgical site was aseptically prepared with provodine-iodine (Wescodyne, West Chemical) followed by 70% ethanol. Six incisions about 1.0 cm each were made in an anterioposterior direction through the skin and subcutis with a scalpel. The incisions were undermined with blunt and sharp dissection to allow implant placement over the superficial epaxial musculature. The nitrocellulose strip containing the rat p65 protein was cut into six pieces (each approximately 0.5 cm×1.5 cm) which were then formed into rolls for insertion. Following placement, the skin edges were opposed with tissue forceps and closed with surgical adhesive (Vetbond, 3M). Adequate spacing (about 2.5 cm) between insertion fields will allow subsequent immunization incisions to be made adjacently. Terminal blood collection was made in Alsever's solution in anesthetized rabbits by the use of a vacuum assisted collection device to provide the serum which is the polyclonal antibody source. The antisera were absorbed with normal plasma proteins immobilized on nitrocellulose sheets following its electrophoresis on 10% SDS-PAGE and transblotting. An ELISA assay or immunoblotting analysis was conducted to determine the potency and specificity of the antisera obtained.

A standard ELISA procedure was used for detection of specific antibodies in serum. Ninety-six well microtiter plates designed for ELISA were used (Immunol 2, Dynatech). For detection of rabbit anti-p65 antibodies, the ELISA plates were pre-coated with several different concentrations of antigen. To test sera, a positive reference serum and a negative pre-immune serum were added to the wells in five-fold dilutions in PBS. Anti-p65 antibodies were detected by goat anti-rabbit IgG conjugated with horse radish peroxidase (Bio-Rad). After the substrate reaction, plates were read on an ELISA plate reader at 405 nm (Litton Bionetics, Laboratory Product Division, S.C.). A serum sample was considered positive when it read 0.05 units or more above the background.

Probing of Western blots with prepared antibody was carried as follows.

The purified rat tumor-associated protein, p65, was separated by PAGE and electrophoretically transferred to nitrocellulose as described above. Free binding sites on the nitrocellulose sheets were then blocked overnight using 1% normal goat serum in TTBs buffer (0.5% Tween, 0.1 mM Tris-HCl, pH 7.1, 09% saline). Antisera obtained from immunized rabbits were diluted serially in the blot buffer (TTBs) and incubated with the nitrocellulose strips for one hour at room temperature. The blots were then washed with several changes of TTBs buffer containing 1% goat serum Bound antibody was detected using biotinylated second antibody (goat anti-rabbit IgG, biotinylated) and the avidinbiotin-peroxidase method (Vectastain ABC Elite, Vector, Burlingame, Calif.). To develop blots, 0.02% hydrogen peroxide was used, mixed with 0.1% diaminobenzidine tetrachloride (DAB) made in 0.1M Tris-HCl buffer, pH 7.2. Color generally developed within five to ten minutes; blots were rinsed with distilled water and air dried to preserve color.

Alternatively, bound antibody was detected by incubating the nitrocellulose strips with $^{125}$I-Protein A ($1\times 10^6$ cpm/ml of blot buffer). After a 60-minute incubation, unbound label was removed by repeated washes of the blots with PBS buffer containing 0.5% Tween. The bound antigen $^{125}$I-Protein A complex was detected by overnight autoradiography using Kodak X-OMAT-AR film.

In addition, monoclonal antibody preparations can be made to the 65 kDa cancer marker by employing conventional techniques well known to the art.

EXAMPLE II

SDS-PAGE and Immunoblotting Analyses

Carefully dissected hepatomas (see Example I) and liver fragments from normal rats and mice were rinsed with an ice-cold saline solution and processed for immunochemical determination of p65. Liver tumor cells grown in culture, as described in Example I, were separated from medium by centrifugation, rinsed with the cold saline solution, and processed for immunoassay of the p65 tumor-associated factor. Briefly, small pieces of tissues or tumor cell pellets were homogenized in TMK-sucrose buffer, pH 7.2, and samples of the total homogenate containing the same amount of protein were mixed with electrophoresis sample buffer, boiled for three minutes, and subjected to 10% SDS-PAGE. The proteins precipitated at 90% saturation of ammonium sulfate from the conditioned medium of hepatocarcinoma cells were dissolved in TMK buffer and electrophoresed in a similar manner. Subsequently, the gel slabs were prepared for transfer by equilibration for one hour in 0.025M Tris, 0.192M glycine, 20% methanol (vol/vol), pH 8.3, and then transblotted onto nitrocellulose sheets.

For immunoassay, the nitrocellulose sheets were treated with the appropriate blocking solution to block non-specific binding sites and incubated overnight, either with pre-immune serum (controls) or antibody against rat p65 diluted 1:200. Secondary biotinylated antibody was applied next, and the color was developed using an ABC Elite Kit (Vector Laboratories, Burlingame, Calif.). The highly specific polyclonal antibody against p65 was obtained by immunizing rabbits with the rat p65 preparation purified as described above.

Presence of p65 in Rat and Mouse Liver Tumors and its Absence from Normal Mouse and Rat Liver When total protein samples from rat and mouse liver carcinomas grown in vitro were analyzed by SDS-PAGE and then anti-rat p65 antibody probing of western blots, a single, prominent band was detected in the 65 kDa region of the blots. Some weak bands seen in the 60–64 kDa region may represent degradation products of the native species of p65. Other minor bands resulted from non-specific staining. There is no band characteristic of p65 in immunoblots representing normal adult rat or mouse liver.

All hepatocarcinoma cells grown in vitro as cell cultures and tumor tissues from Morris hepatomas carried as solid tumors in vivo were positive for the p65 antigen. There was no reaction with normal liver cells of either rat or mouse origin. Thus, immunoblotting analysis has demonstrated that p65 was specifically produced by liver cancer cells but not by the cells of normal adult rat or mouse liver.

EXAMPLE III

Interspecies Cross-reactivity of Antibodies Against p65

The p65 tumor-associated factors derived from different species are immunologically cross-reactive.

TABLE 1

Immunoprecipitation of p65 from Different Sources by Antibodies Raised in Rabbits against Rat p65.

| Source of p65 | Immunoprecipitation of p65[a] |
|---|---|
| Plasma: | |
| Morris Hepatoma 7777-bearing rats | +++ |
| Morris Hepatoma 8994-bearing rats | +++ |
| Pregnant Rats | − |
| Normal Rats | − |
| Cytosol: | |
| Morris Hepatoma 7777 tumors | +++ |
| Morris Hepatoma 8994 tumors | +++ |
| Normal Rat Liver | − |
| Conditioned culture medium: | |
| Morris Hepatoma 7777 cells | +++ |
| Morris Hepatoma 8994 cells | +++ |
| Rat THC 1682 cells | +++ |
| Mouse squamous cell carcinoma | ++ |
| Human breast cancer cells (MCF-7) | ++ |
| Unconditioned culture medium | − |

[a] +++ = over 90% precipitation; ++ = 50-90% precipitation; − = less than 0.5% precipitation.

The p65 activity as measured by the mRNA-transport assay was immunoprecipitated using polyclonal anti-rat p65 antibodies from the serum of rabbits immunized against the rate transplantable hepatocellular carcinoma THC 1682. This antibody removed activity from cytosols derived from Morris Hepatomas 7777 and 8994 and from cell culture media in which tumor cells were grown. Polyclonal anti-rat p65 antibodies reacted with human p65 secreted to the culture medium by the MCF-7 breast cancer cell line. The antibodies also cross-reacted with the mouse p65 factor secreted to medium by mouse squamous cell carcinoma. The p65 tumor-associated factor was not detected in the blood of pregnant rats. It was neither detected in the blood of normal rats nor in unconditioned cell culture medium.

EXAMPLE IV

CNBr Cleavage of p65

Cyanogen bromide (CNBr) cleavage maps of p65 purified from cell culture medium of rat transplantable hepatocellular carcinoma cell line 1682C or mouse liver carcinoma cell line CRL 6421 (MM45) were obtained as follows. p65 preparations (20 μg) purified from cell culture medium were subjected to 12.5% sodium deodecyl sulfate (SDS)-PAGE. The p65 band located on slab gels by Coomassie blue staining of parallel gel tracks was cut from appropriate gel tracks and incubated at room temperature for 16 hours in 1 ml of 88% formic acid containing 20 mg/ml of CNBr. The gel slices were then rinsed five times with 1 ml of water and washed several times for 10 minutes with 1 ml 120 mM Tris-HCl, pH 7.0, 20% glycerol (vol/vol), 2% SDS until the pH of the slices reached 7.0. CNBr-treated gel slices were placed onto 15% SDS-PAGE slabs, electrophoresed, and then stained with silver. Slices of gel containing p65 treated with 88% formic acid served as controls.

Structural Identity of Rat and Mouse p65

Rat and mouse p65 were purified to apparent homogeneity as described above. CNBr cleavage maps were obtained as the first step toward the final characterization of the amino acid composition and sequence of p65. The cleavage of p65 with CNBr resulted in six major peptides identifiable by silver staining of the SDS-PAGE gels. The peptides have molecular weights of about 6, 9, 27, 39, 43 and 47 kDa. Identical cleavage maps were obtained for rat and mouse p65.

EXAMPLE V

Animal Models for Determination of Cancer Risk

The ultimate objective of animal carcinogenicity studies is the determination of possible human risk. The available data show that known human carcinogens that have been adequately studied are also carcinogenic in laboratory animals, often at the same target site. Thus, the identification and elucidation of the mechanisms underlying each stage of the carcinogenic process in animals may offer testable hypothesis for the stages in human. The current tests for cancer risk assessment focus mainly on markers of genetic damage, at the level of the DNA or chromosome, as indicators of genotoxic exposure. These tests, however, are not able to detect the risk associated with exposure to synthetic steroid hormones and other tumor promoters.

It was recently indicated that the promotional status of human subpopulations could be the dominant factor in determining the cancer risk. The development of a more systematic analysis of possible tumorigenesis mechanism has also been suggested. One of the approaches to study in a more systematic way the mechanism of tumorigenesis, involves comparisons among different systems in which tumor induction, or cell transformation has been optimized through the use of the most effective system-specific agents and protocols. When each tumor system is operating optimally, intersystem comparisons could be undertaken with respect to carefully selected biochemical parameters. Tumor-associated proteins, such as the one described herein which appears to be a general marker of preneoplastic and neoplastic alterations, are good candidates to be used in intersystem comparisons.

Monitoring Skin Carcinogenesis with p65 Tumor-Associated Factor

A multistage skin carcinogenesis model was used to monitor the carcinogenic process using the p65 tumor-associated marker.

Skin tumors were induced on the back of SENCAR mice by a single dose of 10 nmol of 7,12-dimethylbenz-[a]anthracene (DMBA) and repetitive applications of 1 μg of 12-O-tetradecanoylphorbol-13-acetate (TPA) twice a week. Blood samples were randomly obtained from four mice at times indicated in FIG. 1. The p65 activity was measured in the blood plasma by use of an ELISA assay.

In a modified ELISA inhibition procedure, 100 μl of purified antigen of predetermined dilution was added to Dynatech Immunon 2 plates and incubated at 37° C. for one hour. This was followed by washing, then binding 1% bovine serum albumin in bicarbonate buffer to cover residual binding sites in the wells. After washing the plates, 100 ml of antiserum plus test samples were added and the incubation carried out for one hour at 37° C. Finally, the immune complex was detected by adding 100 μl of goat/anti-rabbit immunoglobulin conjugated to horseradish peroxidase. Then the substrate 2,2'-Azino-(3-ethylbenzthiazolinesulfonic acid) and 0.03% $H_2O_2$ was added to each well and incubated 10 minutes at room temperature. After terminating the reaction with addition of 20 ml of 2.0 mM $NaN_3$ to each well, the absorbance (405 nm) was read on an ELISA reader.

For convenience of graphing, the inhibition values were changed to units where the sample giving the greatest inhibition will be selected as the end point. The percent inhibition = 100 − [(Absorbance inhibited/absorbance uninhibited) × 100]. The percent inhibition of the sample was multiplied by the reciprocal of the dilution to obtain units of the activity.

Shown in FIG. 1 was the time-course of (A) papilloma appearance and (B) p65 accumulation in the blood plasma. p65 was detected in the plasma at four weeks of promotion, then its activity increased, first slowly up to 20 weeks, and then more rapidly up to 30 weeks, when it began to plateau. p65 was not detected in the blood of non-initiated mice treated with TPA as described above up to 20 weeks (data not shown).

By using a simple blood test for the presence of p65 factor, the skin cancer risk from the tumor promoter TPA can be detected as early as four weeks of treatment with the tumor promoter. A majority of skin papillomas are considered to be non-malignant tumors at early stages of development. Conventional histological and cytogenetic techniques are time consuming and are able to detect skin cancers in mice only at later stages of papilloma development, i.e., at 30–40 weeks.

EXAMPLE VI

Monitoring Liver Carcinogenesis with p65 Tumor-Associated Factor

Altered hepatic foci (AHF) were induced in the course of 2-acetylaminofluorene (AAF)-initiated, phenobarbital (PB)-promoted hepatocarcinogenesis in the rat. Rats (male weanling albinos, Sprague Dawley strain) were purchased from Harlan Labs, Indianapolis, Ind. The 0.06% (w/w) AAF diet and 0.05% PB diet were prepared and pelleted by Altromin, Lage, FRG, and Dyets, Inc., Bethlehem, Pa., respectively. Each of two experimental groups of rats and a control group consisted of 40 rats. All rats entered the experiment at 22 days of age. One group received AAF diet for 18 days, then AIN-76A diet (Dyets, Inc.). The second group received AAF diet for 18 days then AIN-76A diet for 24 days and then AIN-76A diet supplemented with 0.05% phenobarbital. The third group (controls) received AIN-76A diet for 42 days, then AIN-76A diet plus 0.05% phenobarbital.

Immunohistochemical Procedures

The blood and livers of rats (4 animals per each time-point) sacrificed at different times in the course of hepato-carcinogenesis experiment were used for immuno-chemical studies. Paraffin liver sections were prepared and stained with specific antibodies. Polyclonal antibodies to the rat p65, purified to apparent homogeneity, were raised in rabbits as described herein. The p65 was visualized in the liver sections using the avidinbiotin-peroxidase complex (Vectastain ABC Kit, Vector Laboratories, Burlingame, Calif.). Appropriate controls with non-immune serum were performed routinely. Antiserum to p65 was diluted 1:200 in PBS with 1% goat serum for use in the staining protocol. The blood plasma was assayed for the presence of p65 using an LISA assay or PAGE followed by immunoblotting analyses.

The p65 tumor-associated protein was detected in rats fed AAF and PB diets as early as two weeks of feeding with the tumor promoter PB. The p65 marker was predominantly present in the cells of putative pre-neoplastic foci found at 24 weeks of trial in livers of rats fed AAF and PB diets. The p65 marker was highly concentrated in the foci with little or none being detected in the surrounding cells. Either no staining or weak positive staining was found in the areas known for oval and ductular proliferation. No positive staining was found in control livers from normal rats or rats fed only the PB diet. Most of p65 activity appears to be associated with the nuclei of the p65-positive hepatocytes and more precisely with the nuclear envelopes, with relatively little being detected in the cytoplasm. Immunohistochemical staining of the cross-sectioned nuclei revealed that only the periphery of the nuclei, i.e., nuclear envelopes, were stained. These results also affirm the putative role of p65 in the nucleocytoplasmic transport of mRNA.

EXAMPLE VII

Enhancement of p65 Production During Sex Hormone Promotion

Shown in FIG. 2 is the effect of the contraceptive steroid ethynylestradiol (EE), a known tumor promoter in the rat, on the p65 production in female rats initiated with N-methylnitrosourea (MNU), using a protocol designed to induce mammary gland tumors.

A short (one week) exposure to EE at six to seven weeks post-carcinogen treatment, i.e., when the MNU-induced production of p65 was relatively low, caused three-fold increase of the p65 level in the blood plasma. MNU was shown to induce pre-neoplastic foci in the liver; however, they were not detected by the use of the gamma-glutamyl transpeptidase (GGT) assay, even after 23-week promotion with EE. Thus, the p65 production in the rat appears to be extremely sensitive to hormonal stimulation. The high sensitivity of the p65 synthesis during chemical carcinogenesis to sex hormone and phenobarbital promotion indicate that p65 can be used not only as a tumor marker, but also for early assessment of cancer risk associated with the use of synthetic steroids and other drugs that exhibit tumor promotion properties.

It will be apparent to those skilled in the art that numerous changes and modifications can be made in the preferred embodiments of the invention described above without departing from the scope of the invention. Accordingly, the whole of the foregoing description is to be construed in an illustrative and not in a limiting sense, the scope of the invention being defined solely by the appended claims.

What is claimed is:

1. A process for preparing an immunogen of a tumor-associated protein comprising the steps of:
   (a) collecting from plasma, tumor cytosol or ascitic fluid of carcinoma-bearing mammals or from culture medium in which cancer cells were grown, the protein fraction which is precipitated from plasma, tumor, cytosol or ascitic fluid between 30% and 60% saturation of an aqueous ammonium sulfate solution or from culture medium at 90% saturation of an aqueous ammonium sulfate solution, respectively;
   (b) chromatographing the protein fraction on a molecular sieving column and collecting a protein fraction having a molecular weight in the range of about 50 to 90 kilodaltons;
   (c) applying the collected chromatographed protein fraction to a high performance liquid chromatography (HPLC) phenyl hydrophobic interaction column and allowing protein to bind to the column;

(d) eluting the bound protein on the phenyl hydrophobic interaction column with a buffer comprising about 16% ammonium sulfate;

(e) collecting the first distinct protein peak eluted from the column;

(f) electrophoresing the collected protein;

(g) transblotting the electrophoresed protein to a nitro-cellulose sheet;

(h) cutting from the nitro-cellulose sheet that portion which contains a band of protein corresponding to about 65 kD.

2. An antibody preparation comprising antibodies specific to the immunogen of claim 1 and substantially free of antibodies to normal plasma proteins.

3. The antibody preparation of claim 2 which is comprised of monoclonal antibodies.

4. A method for determining the presence in a mammal of a 65 kD tumor-associated protein; the method comprising:

providing antibodies specific for immunogen of claim 1, contacting said antibodies with biological material of said mammal; and determining the presence of an immunological reaction product between said antibodies and said protein.

5. The method of claim 4 wherein the presence of said reaction product is determined by radioimmunoassay, enzyme linked immunosorbent assay, immunoblotting or immunohistochemical staining.

6. The method of claim 4 wherein the biological material is plasma, serum, cytosol fluid, ascites or tissue.

7. The method of claim 4 wherein the biological material is liver tissue or skin.

8. A method for diagnosing a cancer which produces a 65 kD tumor-associated protein in a mammal, comprising:

providing a sample of biological material from said mammal wherein the biological material is plasma, serum, cytosol fluid, ascites or tissue;

contacting said biological material with antibodies specific or the immunogen of claim 1;

determining the presence or absence of an immunological reaction product between said antibodies and the 65 kD tumor-associated protein, the presence of an immunological reaction product being indicative of or an early indication of cancer.

9. The method of claim 8 wherein the biological material is liver tissue or skin.

10. The method of claim 8 wherein the cancer subject to detection is liver cancer, breast cancer, skin cancer or squamous cell carcinoma.

* * * * *